United States Patent [19]
Killion

[11] Patent Number: 4,852,683
[45] Date of Patent: Aug. 1, 1989

[54] EARPLUG WITH IMPROVED AUDIBILITY

[75] Inventor: Mead C. Killion, Elk Grove Village, Ill.

[73] Assignee: Etymotic Research, Inc., Elk Grove Village, Ill.

[21] Appl. No.: 148,939

[22] Filed: Jan. 27, 1988

[51] Int. Cl.[4] .................... G10K 11/00; H04R 25/02
[52] U.S. Cl. .................................. 181/130; 181/132; 181/135
[58] Field of Search ............... 181/130, 134, 135, 132, 181/129, 22; 128/152; 381/68.6, 154

[56] References Cited

U.S. PATENT DOCUMENTS

| Re. 29,487 | 12/1977 | Gardner, Jr. | 128/152 |
|---|---|---|---|
| 3,565,069 | 2/1971 | Miller | 128/152 |
| 3,800,101 | 3/1974 | Milani | 381/187 X |
| 4,349,082 | 9/1982 | Gastmeier | 181/130 |

OTHER PUBLICATIONS

Killion et al., *The Hearing Journal*, "An Earplug with Uniform 15-dB Attenuation", 1988, vol. 41(5), pp. 14-17.
*Etymotic Research*, "Tubephone, ER-3A Insert Earphone", Aug. 1987, data sheet.
*The Etymotic Update*, "Progress Report on ER-15 Musician's Earplug", Dec. 1988, pp. 1-2.
*Fortune*, "Great Moments in Workplace Safety", Jan 18. 1988, pp. 165, 168.
E. H. Berger et al., *Noise and Hearing Conservation Manual*, "Auditory Effects of Noise", 1986, pp. 197, 204-208.
E. H. Berger et al., *Noise and Hearing Conservation Manual*, "Audiometric Data Base Analysis", 1986, pp. 293, 314-315.
Killion, *Journal of Speech and Hearing Disorders*, "Earmold Options for Wideband Hearing Aids", 1981, pp. 10-20.

Primary Examiner—B. R. Fuller
Attorney, Agent, or Firm—Neuman, Williams, Anderson & Olson

[57] ABSTRACT

An earplug uses damping to render unimportant a Helmholtz resonance between the acoustic mass intrinsic to a sound channel thereof and the compliance of air in the earcanal unimportant, in combination with an external structure coupled to the sound channel to increase response characteristics at higher frequencies in a predictable and well controlled manner in order to provide a highly desireable uniform frequency response.

19 Claims, 7 Drawing Sheets

EARPLUG WITH IMPROVED AUDIBILITY

BACKGROUND OF THE INVENTION

1. Field of the Invention

This invention relates to improved devices for providing hearing protection from exposure to sounds that are intense enough to risk hearing damage.

2. Background of the Prior Art

It is well documented that repeated or prolonged exposure to sounds of sufficiently high sound pressure level (SPL) will cause temporary or permanent hearing loss. A good summary of research in this field can be found in the book Noise & Hearing Conservation Manual, Fourth Edition edited by E.H. Berger, W.D. Ward, J.C. Morrill, and L.H. Royster and published by the American Industrial Hygiene Association, Akron, OH (1986). The chapter "Auditory Effects of Noise" written by W. D. Ward is particularly recommended. The application of hearing protection in the form of earmuffs or earplugs is commonly employed to reduce the SPL reaching the ear, thereby preventing hearing loss. ANSI standard S12.6-1984 (American National Standards Institute, N.Y., N.Y.) describes the accepted Real Ear Attenuation at Threshold method for measuring the amount of reduction in SPL reaching the eardrum that results from the application of a particular earmuff or earplug.

Earplugs and earmuffs suitable for preventing hearing loss are widely available. An earplug that is widely used for hearing conservation in industry is the slow-recovery foam earplug described in Reissue Pat. No. 29,487 Reissued Dec. 6, 1977, and manufactured by the E-A-R Division of Cabat Corporation. This plug, trademarked as the E-A-R plug has been demonstrated to be highly effective in preventing hearing loss as summarized by J.D. Royster and L.H. Royster in their chapter "Audiometric Data Base Analysis" in the aforementioned book. When properly inserted, the E-A-R PLUG provides approximately 35 dB of attenuation at low frequencies and approximately 45 dB of attenuation at high frequencies. Similar high frequency attenuation values have been reported for other well-sealed earplugs including custom earmolds fabricated specifically for hearing protection. Although such large attenuation values are required for protection against exceedingly high sound pressure levels such as near jet aircraft or the like, more common working environments may require only 10 to 20 dB of attenuation in order to be safe.

Earplugs of the foregoing type have had certain inherent disadvantages. In applications where the user wants or needs to hear clearly, the high-frequency attenuation provided by the foregoing earplugs is excessive, resulting in a muffled sound. One example is provided by the mechanic in a moderately noisy factory who must listen to the sound of the machinery in order to monitor proper operation or diagnose the likely source of malfunction. Another is the musician in a confined rehearsal or performing space who must listen to the sound of the other musicians in order to play properly. It is well known that individuals in both situations routinely refuse to wear hearing protection. A recent news item in the Jan. 18, 1988 issue of Fortune magazine reported a Colorado high school district edict requiring band directors to wear hearing protection because of worker compensation cases, and further reported the incredulous refusal of the band directors to do so: "It's difficult enough to provide music on a competent level with your ears wide open ..." one was quoted as saying.

Earplugs providing less high frequency attenuation have been known. Extensive real ear attenuation measurements on 21 brands of earplugs were reported by J.B. Tobias, for example, in FAA report FAA-AM-73-20 (Washington, D.C., 1973). In all cases, earplugs with reduced attenuation at high frequencies provided little or no low frequency attenuation, again resulting in an unnatural sound somewhat similar to the sound of a high-fidelity record player with the bass turned up and the treble turned all the way down.

Most recently, high-fidelity earplugs suitable for use with custom earmolds have been introduced by Etymotic Research, Inc., licensed under a patent application to be filed by Elmer Carlson. These earplugs provide a uniform attenuation of approximately 15 dB across nearly the entire audible frequency band, from 20 Hz to at least 10 kHz, as confirmed by applicants own measurements. These earplugs include:

1. A flexible diaphragm as a series compliance element to provide a pressure divider with the compliance of the earcanal volume, resulting in a uniform low frequency attenuation, 2. An internal acoustic sound tube as a mass reactance element to series resonate with the compliance of the earcanal volume at approximately 2700 Hz, preserving the relative frequency response characteristics of the sound-field-to-eardrum-pressure transfer function of the normal external ear which has an approximately 15 dB peak at approximately 2700 Hz, 3. An internal series damping resistance element to limit the amplitude of the aforementioned resonance peak at 2700 Hz to approximately 15 dB, further preserving the relative frequency response characteristics of the sound-field-to-eardrum-pressure transfer function of the normal external ear which has an approximately 15 dB peak at approximately 2700 Hz, and 4. A distributed acoustic network to provide a low impedance shunting of acoustic energy at approximately 8000 Hz where the earplug attenuation would otherwise be reduced to a low value because the distance between the sound outlet of the earplug and the eardrum is nearly a half wavelength resulting in the formation of a half wave resonance condition in the earcanal at that frequency.

Although the Carlson earplug represents an important and substantial contribution, it has limitations which have not been recognized. The cost of manufacture thereof is relatively high, precision manufacture of the various acoustic elements being required in order to obtain the desired uniform attenuation frequency response. An additional limitation of the Carlson earplug is that it requires use of a precise and relatively large diameter and short length internal sound tube in the accompanying custom earmold. Depending on the sound tube length that is chosen, internal diameters of 3 to 5 mm are required for the sound tube in order to obtain the value of mass reactance needed for proper operation of the Carlson earplug. Such a requirement is not readily compatible with the use of a slow recovery foam eartip in order to make a "universal" ready-to-use version; it is found that a tube with about 2 mm inner diameter is the largest practical tube for use in a "universal" eartip. For example, a commercially available Etymotic Research ER3-14 eartip used with the Etymotic Research ER-3A audiometric earphone for hearing testing, uses a tube with a 1.93 mm internal diameter. In the ER3-14 eartip, one end of the tube is inserted into a central opening of a slow recovery foam member which has a diameter of about 18 mm and a length of about 12 mm, the tube having an opposite end coupled through a longer tube to the audiometric earphone.

A further limitation associated with the relatively short sound tube required with the Carlson earplug is that the eartip will itself also be naturally short, resulting in a seal to the ear close to the entrance of the earcanal. As a consequence, the Carlson earplug will be susceptible to a large occlusion effect as described in the article "Zwislocki was right...A potential solution to the 'hollow voice' problem (the amplified occlusion effect) with deeply sealed earmolds" by M.C. Killion, L.A. Wilber, and G.I. Gudmundsen (Hearing Instruments, January, 1988). Thus the user will experience his own voice as having a "hollow sound" due to the unusually large eardrum SPL's that will be developed at low frequencies whenever he talks, and the user will be unable to understand other people talking due to the masking effect of the unusually large eardrum SPL's that will be developed whenever he chews corn chips or other crisp foods.

SUMMARY OF THE INVENTION

It is an object of the present invention to provide a more economical earplug exhibiting relatively uniform attenuation throughout the 500 Hz to 6000 Hz frequency range important to speech intelligibility. In particular, it is an object of the present invention to provide an economical earplug whose real ear attenuation at the higher speech frequencies does not appreciably exceed its real ear attenuation at the lower speech frequencies.

Another object of the present invention is to provide an economical earplug exhibiting relatively uniform attenuation throughout most or all of the audible range of frequencies.

It is a further object of the present invention to provide an earplug that uses inexpensive commercially available ready-to-use slow-recovery foam eartips such as the aforementioned ER3-14 eartip or a shortened version thereof or the like.

It is a further object of the present invention to provide an earplug that permits the seal to the ear to occur deeply in the earcanal to reduce or eliminate the occlusion effect and permit the user to experience his own voice in a more natural manner.

These and other objects and features are achieved in the present invention through the use of an earplug construction in which an assembly contains an acoustic damper between two sound tubes, the first being the sound tube internal to the eartip and the second being an external sound tube that has a one-quarter-wavelength resonance at approximately 2700 Hz and is arranged so that its external inlet is placed near the sealed entrance to the earcanal. By suitable choice of a relatively large damping resistance, the resonance between the mass reactance of the internal sound tube and the compliance of the earcanal volume is completely damped, so that the length and diameter of the internal sound tube becomes relatively unimportant. This permits the use of a relatively long internal sound tube with relatively small internal diameter and, in particular, permits proper operation in conjunction with the use of a type of eartip having a relatively small internal diameter tube and which is otherwise practical and desirable, such as the aforementioned ER3-14 eartip. An ER3-14 eartip, in turn, may readily be sealed deeply in the earcanal, reducing or eliminating the occlusion effect as directly verified in the occlusion effect experiments reported in the aforementioned Killion et al article.

An additional benefit to the use of a relatively large damping resistance is that more low frequency attenuation is obtained, relative to a given high frequency attenuation, than is obtained with conventional moderate-attenuation earplugs where the dominant attenuating impedance throughout much of the frequency range is that of a mass reactance.

In the present invention the increased high frequency attenuation resulting from the use of a relatively large damping resistance as described above is partially compensated for by locating the external sound inlet deeply in the concha of the ear, where an increased sound pressure level is produced in the 2 to 10 kHz range of frequencies due to resonances caused by the structure of the concha and the pinna of the ear, as described by E.A.G Shaw in his chapter "*Acoustics of the External Ear*" in the book *Acoustical Factors Affecting Hearing Aid Performance* edited by G.A. Studebaker and I. Hochberg (University Park Press, Baltimore MD, 1980).

A further improvement in high frequency performance is obtained in the present invention by the novel use of an external sound tube which has an internal diameter larger than that of the internal sound tube, so that a high frequency "Horn Effect" is obtained, resulting in an increased transmission of the high frequency sounds. This effect is described in the article "*Earmold Options for Wideband Hearing Aids*" by *M.C. Killion* appearing in the *Journal of Speech and Hearing Disorders* 46, 10–20 (1981).

In another embodiment, the above-described earplug is combined with a flexible diaphragm acting as a series compliance element, in a manner similar to that employed in the Carlson earplug, in order to extend the frequency range of uniform attenuation down to the lowest audible frequencies.

This invention contemplates other objects, features and advantages which will become more fully apparent from the following detailed description taken in conjunction with the accompanying drawings.

DESCRIPTION OF PREFERRED EMBODIMENTS

Figure 1:
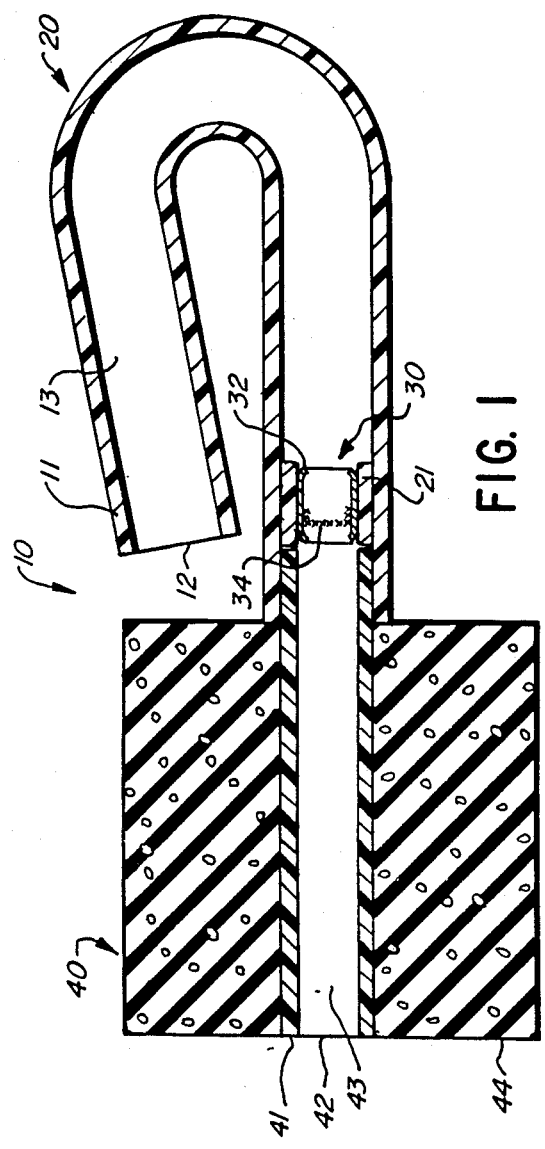
FIG. 1 is a cross-sectional view of the earplug assembly in its simplest form constructed in accordance with the present invention and combined with a slow-recovery-foam eartip.
Figure 3:
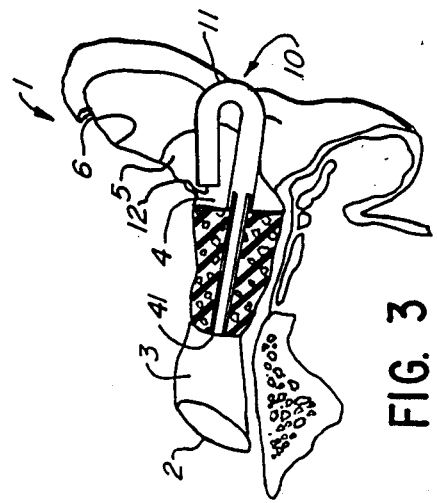
FIG. 3 is a cross-sectional view of the earplug assembly of FIG. 1 properly positioned in an ear.
Figure 4:
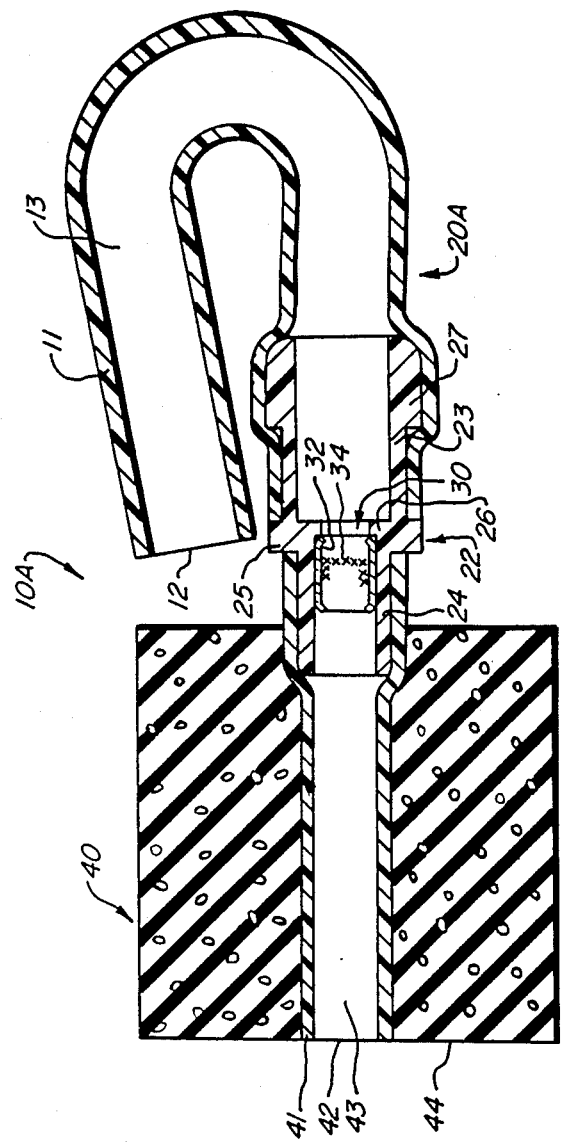
FIG. 4 is a cross-sectional view of another version of the earplug assembly constructed in a form suitable for mass production and distribution in accordance with the present invention.

The devices of this invention are designed for use with a human ear which is designated by reference numeral 1 in FIG. 3 and which includes an eardrum 2, an ear canal 3 with an entrance 4 thereto, a concha or shell-like structure 5 around the entrance 4 and a pinna or external ear structure 6. One embodiment of an earplug assembly of the invention is shown in FIGS. 1 and 3 and is generally designated by reference numeral 10. Another similar embodiment is shown in FIG. 4 and is generally designated by reference numeral 10A. In both embodiments, an external sound tube 11 is provided which has an external opening 12 and an internal sound channel 13, to form part of an attenuating sub-assembly 20 adapted to be positioned within the pinna 6 as shown in FIG. 3. The illustrated tube 11 has a generally U-shaped configuration. The external opening 12 at one end thereof forms a sound inlet for the earplug 10 and is located within the concha 5 and at a position very close to the entrance 4 of the ear canal 3. An internal opening at the opposite end of tube 11 is also positioned within the concha 5, at a position opposite the ear canal entrance 4, to be coupled thereto through eartip subassemblies of different forms and through adapter tubes of different forms.

In FIG. 1, an adapter tube 21 is provided which is simply a short length of tubing disposed within the tube 11. In FIG. 4, a more rugged adapter tube 22 is provided which includes outer and inner coupling sections 23 and 24 at opposite ends thereof separated by a central larger diameter annular portion 25 on the outside and by a reduced diameter annular portion 26 on the inside. Section 23 is disposed within one end of the external sound tube 11 and has a larger diameter terminal end portion 27 for stretching the tube 11 and resisting withdrawal of the adapter tube 22 from the tube 11. Preferably, the dimensions and materials of the parts are such that the tube 11 is stretched in a manner as shown to provide a substantially unbroken and uniform diameter sound channel at the junction between tube 11 and the outer coupling section 23.

A damper assembly 30 is disposed within the short adapter tube 21 of FIG. 1 or within the coupling section 24 of adapter tube 22 of FIG. 4. The illustrated damper assembly 30 includes a thin-walled support ring 32 which has an outer end abutting the inside annular portion 26 of tube 22 and which supports a damping resistance element 34 in the form of a fine screen. It will be understood that other forms of resistance elements or damping means may be employed.

Figure 2B:
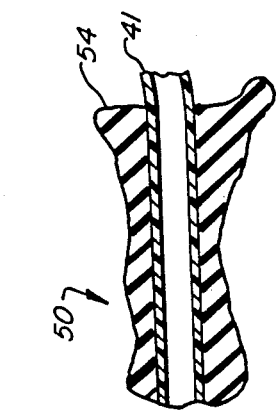
FIG. 2B is a cross-sectional view of a custom earmold assembly to illustrate one of the alternate coupling methods possible with the earplug of the present invention.
Figure 2A:
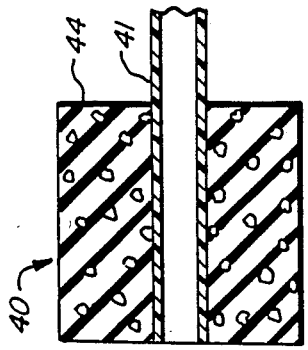
FIG. 2A is a cross-sectional view of the disposable slow recovery foam eartip assembly that may be employed.

In both FIGS. 1 and 4, and also in FIG. 2A, an eartip subassembly 40 is illustrated which includes an inner sound tube 41 having an inner outlet end 42 and an inner sound channel 43, a foam eartip 44 being cemented or otherwise secured on the outside of tube 41. In FIG. 1, the outer end of tube 41 is disposed within the terminal end of the external sound tube 11 and it abuts the short adapter tube 21 which is disposed within the external sound tube 11. In FIG. 4, the outer end of the tube 41 surrounds the inner coupling section of the adapter tube 22 and is preferable stretched, as shown, so as the provide an unbroken uniform diameter sound channel at the junction between tube 41 and coupling section 24.

FIG. 2B illustrates an alternative form of eartip assembly 50 in which a custom earmold 54, formed after taking an impression of the ear of a user, is cemented or otherwise secured to the tube 41.

In both of the embodiments of FIGS. 1 and 4, an inner passage of substantially uniform diameter extends within the internal sound tube 41 from the inner end of the eartip assembly to the outer end of the ring 32 of the damper element 30 and an outer passage, also of substantially uniform diameter, extends from the outer end of the ring 32 of the damper element 30 and within the external sound tube 11 to the outer end 12 of tube 11 which forms a sound inlet to the earplug. The diameter of the outer passage is greater than that of the inner passage to provide a highly desirable "horn effect" or "horn action" as hereinafter described.

In constructing the devices 10 and 10A, the outer or external sound tube 11 may typically be formed from a 36 mm. length of #10 vinyl tubing having an inside diameter of 0.106 inches and an outside diameter of 0.138 inches. A wide variety of other materials having generally similar dimensions can also be used. For example, slightly better high frequency performance can be obtained if #9 vinyl tubing is used rather than #10 tubing in the assembly 10A of FIG. 4. Damper assembly 30 may be made as described by Carlsen and Mostardo in Pat. No. 3,950,560 and which is commercially available as the Knowles Electronics, Inc. 1500 Ohm BF-1861 damper, for example.

The eartip subassembly 40 of FIGS 1, 2A and 4 may use a plug of foam plastic, of a type marketed under the trade name "E-A-R", in which a hole has been formed to accept the inner sound tube 41 which may typically be formed from #13 vinyl tubing having an inside diameter of 0.076 inches and an outside diameter of 0.109 inches. With this construction, the eartip assembly 40 is a shortened version of an Etymotic Research ER3-14 eartip, with a resulting total length of 16 mm for inner sound tube 41. With the alternate method of sealing to the ear shown in FIG. 2B, the earmold assembly 50 is obtained by taking an impression of the ear and sending it to a hearing aid earmold laboratory in the customary manner to obtain the custom earmold 54 with the tubing 41 being unbent #13 vinyl tubing 41 cemented in place. For minimum occlusion effect as discussed by Killion, Wilber and Gudmundsen, the fitter in this case would order a soft vinyl "canal tip" style earmold with tubing 41 cut to extend approximately 4 mm out of the earmold. It will be understood that any method of sealing to the ear may be used which includes an inner sound channel equivalent to a section of #13.

FIG. 3 illustrates the proper location of the complete earplug assembly 10 of FIG. 1 in the earcanal 3 of a the illustrated ear 1, applicable also to the assembly 10A of FIG. 4. The sound inlet 12 of the external sound tube 11 is located as close as possible to the entrance 4 of the earcanal so that the increased sound pressure level or "SPL" developed by resonances in the cavities formed by the concha 5 and the pinna 6 will be made available at sound inlet 12. Note that because of the overlap of external sound tube 11 and internal sound tube 41 the effective acoustical sound channel of external sound tube 11 is approximately 30 mm in length. Due to the "end effect" introduced by the reactive component of the radiation impedance seen looking out from the end 12 of the external sound tube 11, the effective acoustical length of external sound tube 11 is approximately 32 mm, so that a quarter-wave resonance boost is obtained at approximately 2700 Hz (frequency in Khz=one-fourth the velocity of sound in thousands of mm. per second divided by the length in mm.=86/32=2.687 kHz). Similarly, the increased cross-sectional area of external sound tube 11 over that of internal sound tube 41 provides a broadband increase in sound pressure level above about 3 kHz due to "horn action" acting to improve the coupling between the relatively low acoustic source impedance presented by the free air in the vicinity of the earcanal entrance 4 and the relatively high acoustic load impedance presented by the air in the earcanal 3. Both the quarter-wave and horn-action phenomena are reviewed in the appendix of my aforementioned article "Earmold options for wideband hearing aids", the disclosure thereof being incorporated herein by reference.

Figure 5:
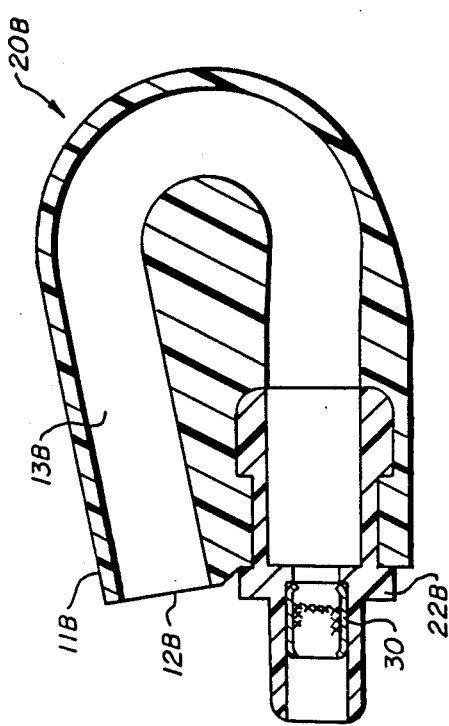
FIG. 5 is a cross-sectional view of still another version of the earplug assembly constructed in accordance with the present invention.

FIG. 5 shows a modified attenuating subassembly 20B wherein external sound tube 11 has been replaced by a molded plastic assembly 11B which provides an external opening 12B and a generally U-shaped or reversely bent internal sound channel 13B, assembly 20B being cemented or welded to or formed integrally with a molded adapter 22B. It will be readily appreciated that the embodiment of FIG. 5 is readily and economically manufacturable in large quantities.

Figure 6B:
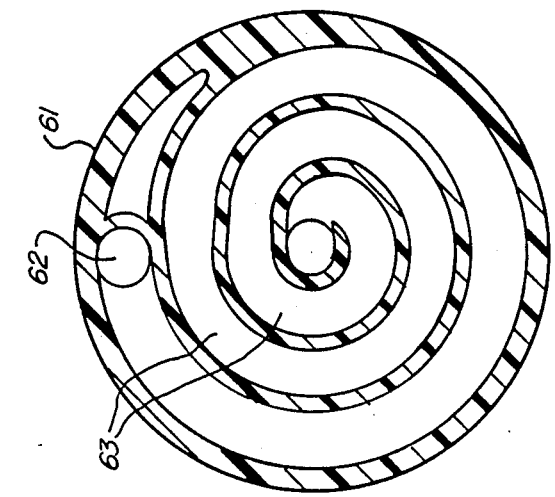
FIGS. 6A and 6B are longitudinal and transverse cross-sectional views showing a further version of earplug assembly constructed in accordance with the present invention.
Figure 6A:
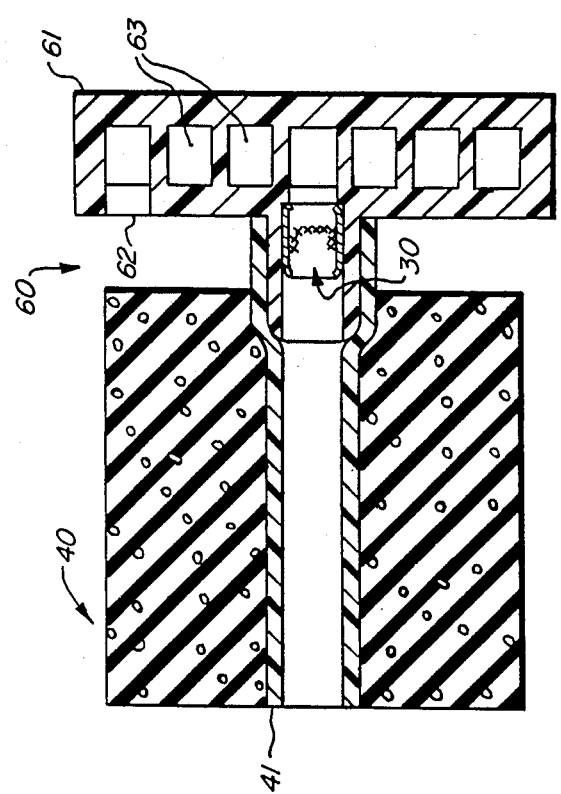

FIGS. 6A and 6B show a complete earplug assembly 60 wherein molded labyrinth member 61 is provided which houses damper assembly 30 and is the acoustical equivalent of, and combines the functions of, external sound tube 11 and adapters 21 or 22 of FIGS. 1 and 4. The member 61 provides an external opening 62 and a sound channel 63 which spirals inwardly from the opening 62 to an inner end at the damper assembly 30. The length and cross-sectional area of sound channel 63 are such as to provide the same one-quarter-wave resonance at approximately 2700 Hz and the same horn effect as is provided by external sound tube 11 of FIGS. 1 or 4. This embodiment may fit more compactly within the pinna of the ear and may permit more compact and attractive packaging.

Figure 7:
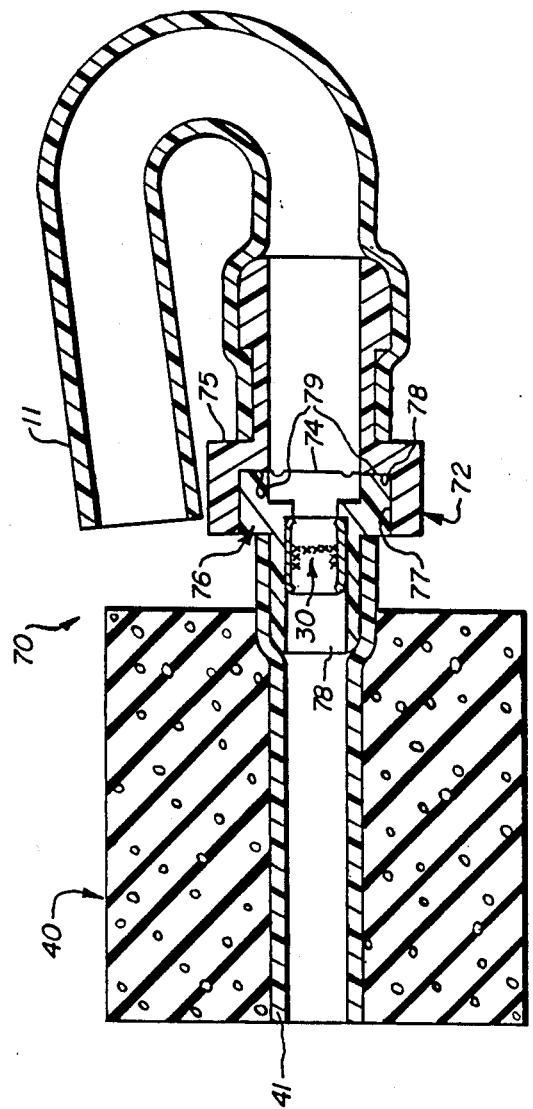
FIG. 7 is a cross-sectional view of a version of an earplug assembly that includes a flexible diaphragm compliance element and is constructed in accordance with the present invention.

FIG. 7 shows an earplug 70 in which an adapter tube 72 supports a flexible diaphragm 74 which is added as a series acoustic compliance element to provide increased attenuation at very low frequencies. The operation differs from the operation obtained with a diaphragm in the aforementioned Carlson earplug, in that in the earplug 70, the resonance resulting from the combination of mass reactance of tube 41 and the compliance of the ear canal is completely damped by the resistance of damping assembly 30 and the diaphragm serves only to increase attenuation at low frequencies, whereas in the Carlson earplug the compliance of the diaphragm also cooperates with the mass reactance of the tube within the eartip to reduce attenuation by producing a resonance peak at 2700 Hz, the damping element being provided for the purpose of limiting that peak.

In practice, the adapter tube 72 may be formed in two separate sections 75 and 76, section 75 being formed to provide a socket 77 and an annular shoulder 78, an end portion of section 76 being inserted into the socket 78 to sandwich a peripheral edge portion of the flexible diaphragm 74 between the terminal end of section 76 and the shoulder 78. Increased ease of handling of flexible diaphragm 74 may be obtained by first cementing the peripheral edge portion thereof to a thin washer 79 which may be stamped from any rigid material.

Figure 8:
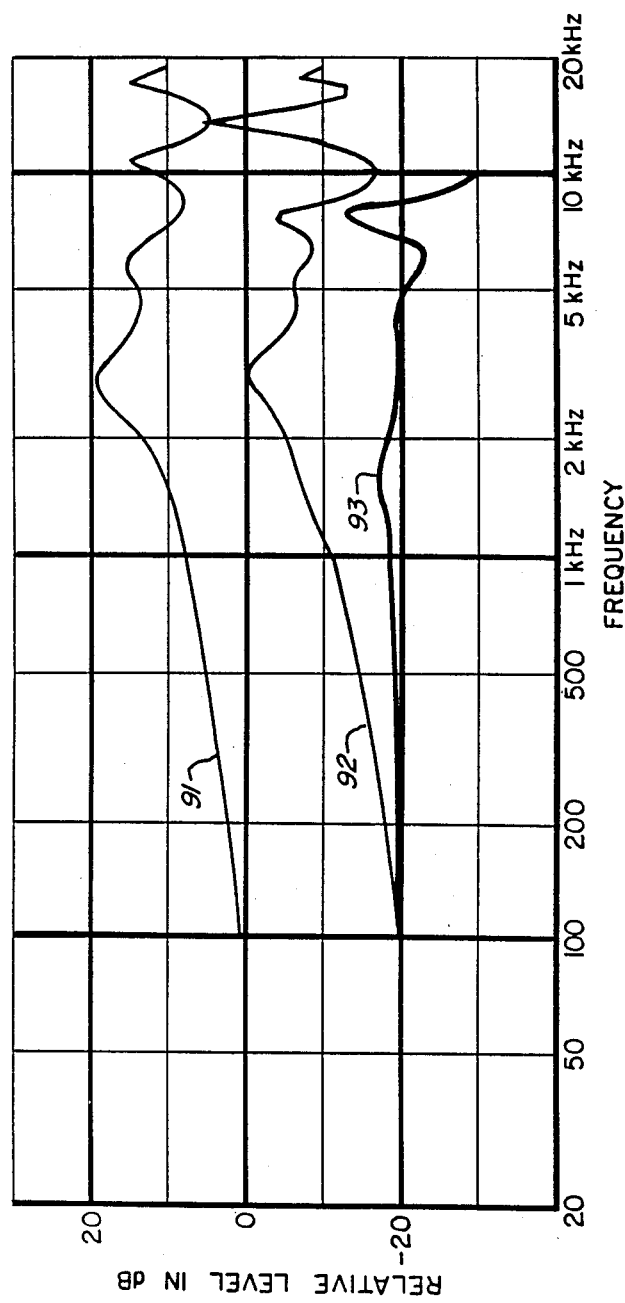
FIG. 8 is a graph showing and comparing the frequency response characteristics of a earplug assembly of the invention, such as the assembly of FIG. 7, with those of an open ear.

FIG. 8 is a graph in which the relative sound pressure level in decibels is plotted verses frequency. Curve 91 is the response at the eardrum with an open ear and curve 92 is the response with the earplug 70 of FIG. 7. Curve 93 is a relative response curve representing the difference between curves 91 and 92 and is thereby an earplug attenuation curve. These curves were obtained by calculations which assumed a 90 degree sound field, a compliance of 0.1 acoustical microfarads for the diaphragm 74 and a resistance of 1500 acoustical ohms for the damping element 30. The internal tube 41 was asssumed to have a length of 16 mm and an internal diameter of 1.93 mm and the external tube 11 was assumed to have a length of 32 mm and an internal diameter of 3 mm. Under the assumed 90 degree sound field condition both curves 91 and 92 show somewhat greater response than would be expected in tests in a diffuse sound field as specified in the aforementioned ANSI standard S12.6-1984. For example, the peak of the open ear response is shown to be nearly 20 dB whereas a peak of about 15 dB would be expected in such tests in a diffuse sound field. However, the difference curve 93 is quite accurate and it illustrates that a very uniform 20 dB attenutation is obtained over the entire range from 100 Hz to over 5000 Hz.

Figure 9:
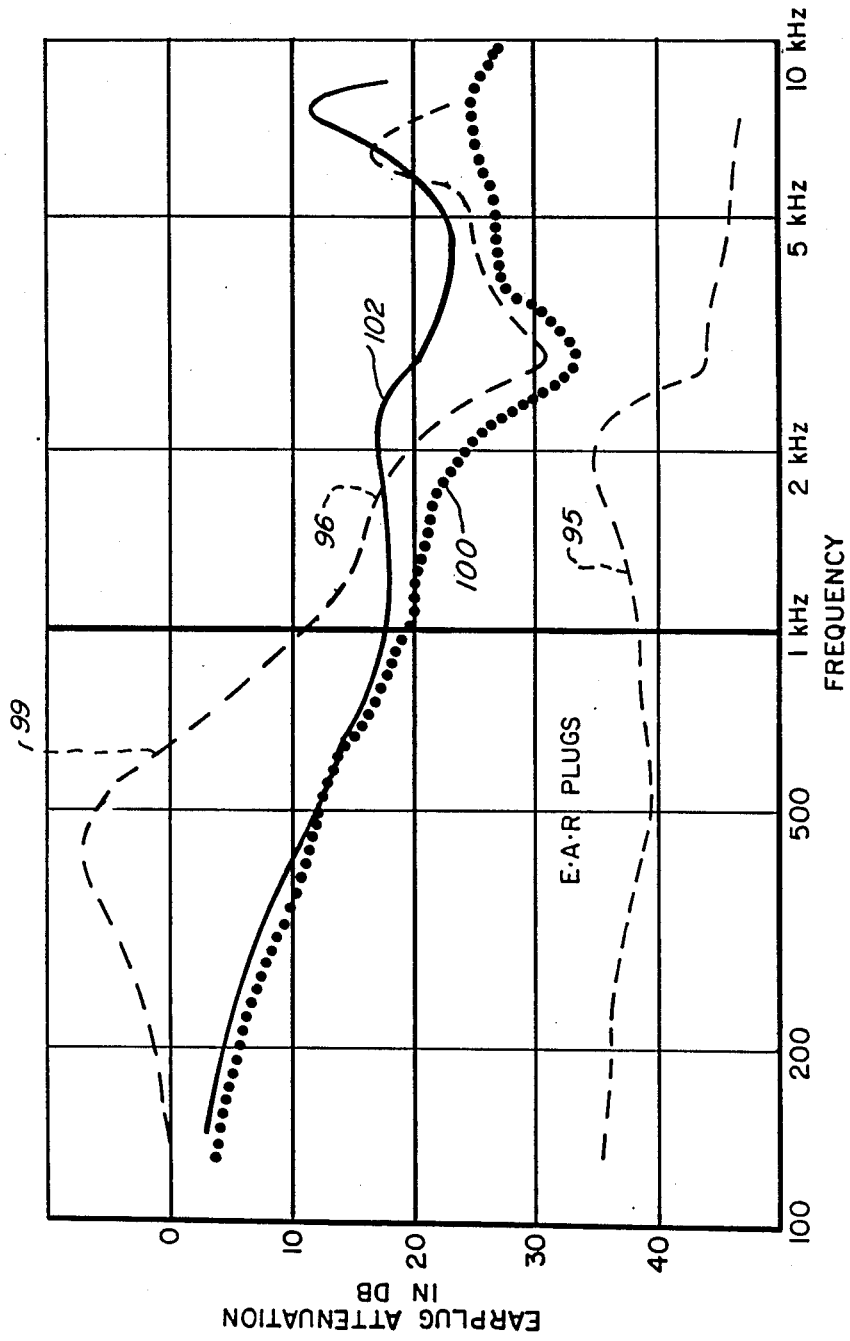
FIG. 9 shows the real ear attenuation frequency response curves of various earplug configurations for explanation of the operation of earplugs of the invention.

FIG. 9 is a graph with relative response curves similar to the relative response curve 93 of FIG. 8 but with various earplug configurations, the purpose being to illustrate the functions of the various components of the earplugs and to show how they cooperate in producing the desired advantageous results. Each of the curves of FIG. 9 represents results of actual tests.

Curve 95 shows the published real ear attenuation of the aforementioned slow-recovery foam E-A-R plugs when properly inserted. As discussed above, their high frequency attenuation of approximately 45 dB is too great for many applications and makes critical listening difficult.

Figure 10:
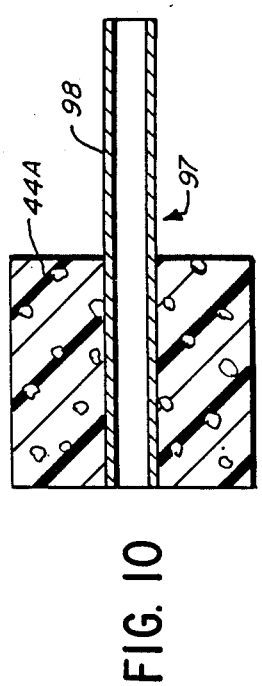
FIG. 10 shows an earplug configuration used in developing one of the response curves of FIG. 9.

Curve 96 shows the attenuation of the aforementioned ER3-14 eartip used "as is" as an earplug 97 as depicted in FIG. 10. In the ER3-14 eartip, as shown, one end of a tube 98 is inserted into a central opening of a slow recovery foam member 44A which has a diameter of about 18 mm and a length of about 12 mm, the tube 98 having an internal diameter of 1.93 mm, an overall length of about 25 mm and having an opposite end which would normally be coupled through a longer tube to a audiometric earphone. With respect to curve 96, note that not only is the high frequency attenuation of such an earplug still too great for some applications, but a new and undesirable resonance peak 99 has been introduced at about 400 Hz so that SPL's in that frequency region are increased rather than attenuated. The result is an unnatural, "boomy" sound that is most unpleasant. Even so, the lessened high frequency attenuation offered by placing a sound channel through the earplug is sufficiently important to some users that they have been willing to sustain the unnatural sound introduced by the resulting resonance. To one degree or another, curve 96 represents many of the commercially available custom earplug designs, although a restriction somewhere in the sound channel is usually introduced to provide some damping of the resonance peak.

Figure 11:
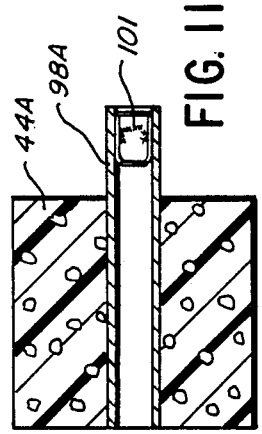
FIG. 11 shows another earplug configuration used in developing another of the response curves of FIG. 9.

Curve 100 shows the improvement in attenuation characteristic over curve 96 that is obtained by reducing the length of the ER3-14 eartip of FIG. 10 to provide a shortened tube 98A as shown in FIG. 11, a 1500 ohm damping element 101 being inserted into the shortened tube 98A. This embodiment is thus similar to the embodiments of FIGS. 1, 4, 5 and 6 with the external tube removed. The low frequency resonance peak 99 of curve 96 has been removed with this embodiment but an attenuation peak remains in a range centered at about 2500 to 3500 Hz.

Curve 102 of FIG. 9 shows the improvement in attenuation characteristic obtained by following the teachings of the present invention, using the embodiments of FIGS. 1, 4, 5 or 6 in which an external tube is included which has an appropriate length to restore the normal resonance peak at 2700 Hz and which has a cross-sectional area such as to obtain horn action, and wherein the sound inlet is arranged to pick up sound in the concha as illustrated in FIG. 3. This improvement provides a nearly uniform attenuation over the important speech frequencies from 500 Hz to 6000 Hz.

When the diaphragm 74 of FIG. 7 is added, the effect is to increase attenuation in the low frequecy range below 1000 Hz and to change from a response as depicted by reference numeral 102 in FIG. 9 to a response as depicted by reference numeral 93 in FIG. 8. It is noted however that in many applications a response as depicted by reference number 102 may be quite adequate and the addition of the diaphragm 74 may be unnecessary or even undesirable.

All of the earplugs of the invention have very important advantages in that components of standard, readily available types are used. No special precision components or difficult and critical assembly operations are required and the earplugs are readily and economically manufacturable. They fit unobtrusively into the ear and can be worn comfortably for extended periods. The tubes within the foam members have standard diameters which are relatively small in relation to the inside diameter of an ear canal to avoid undue compression of the foam members and to avoid exertion of undue pressures on the walls of the ear canal. At the same time, the earplugs provide excellent performance characteristics, producing attenuations such as to protect the ear while allowing the user to hear naturally and with high fidelity, but at reduced amplitude, those sounds which he or she desires to hear.

It is further noted that with the earplug constructions of the invention, the response characteristics can be readily changed to match the requirements of particular users. For example, if it is desired to obtain a response peak at a frequency higher or lower than the typical frequency of 2700 Hz, it can be accomplished by simply decreasing or increasing the length of the external passage.

It will be understood that other modifications and variations may be effected without departing from the spirit and scope of the novel concepts of this invention.

I claim:

1. A protective earplug with improved audibility, comprising: first passage means arranged for positioning with at least an inner end portion thereof in an earcanal to define a first sound passage extending from an inner end within the ear canal to an opposite outer end, a relative large acoustic resistance means arranged for cooperation with an intrinsic acoustic mass reactance of said first passage and an intrinsic acoustic compliance of the ear canal to provide a substantially non-resonant acoustic impedance, and second passage means defining a second sound passage having an inner end coupled to said outer end of said first passage and having an opposite sound-receiving outer end, said second passage being operative to increase response characteristics at frequencies in an audible spectrum above approximately 800 Hz.

2. An earplug as defined in claim 1, said second passage having a length of approximately one-fourth wavelength at a frequency at which the response of the ear is at a maximum.

3. An earplug as defined in claim 1, said outer end of said second passage forming a sound inlet for said earplug and being positioned in proximity to an entrance to the earcanal.

4. An earplug as defined in claim 3, said second passage having a reverse bend therein.

5. An earplug as defined in claim 3, said second passage having a spiral shape.

6. An earplug as defined in claim 1, said first passage means comprising a generally straight tube, and a compressible foam member surrounding said tube.

7. An earplug as defined in claim 6, said tube having an outside diameter which is a small fraction of an inside diameter of the earcanal.

8. An earplug as defined in claim 1, wherein said second passage provides a horn effect.

9. An earplug as defined in claim 8, wherein each of said first and second passages is of uniform cross-sectional size, said second passage having a cross-sectional size greater than that of said first passage to obtain said horn effect.

10. An earplug as defined in claim 1, said acoustic resistance means comprising foraminous means positioned in proximity to said outer end of said first passage.

11. An earplug as defined in claim 1, further including acoustic compliance means in series relation to said first and second passages and operative to increase attenuation in a lower portion of the audible spectrum.

12. An earplug as defined in claim 11, said acoustic compliance means comprising a diaphragm positioned in proximity to the inner end of said second passage.

13. A protective earplug with improved audibility, comprising: an eartip assembly for insertion in an earcanal and constructed and arranged to produce an attenuation of audible sounds which increases with frequency within a major portion of an audible spectrum above approximately 50 Hz, and an external structure connected to said eartip to be positioned within an outer ear and defining a sound inlet for said earplug and a passage extending from said sound inlet to said eartip assembly, said passage being operative for enhancing response at audible frequencies above approximately 800 Hz to obtain a more uniform attenuation of sounds by the earplug over the aforesaid audible spectrum above approximately 50 Hz.

14. An earplug as defined in claim 13, wherein said eartip assembly comprises a generally cylindrical member of compressible foam material having a central opening therethrough and a tube having an inner end portion disposed in said opening, an outer end of said tube being coupled to an inner end of said passage of said external structure.

15. An earplug as defined in claim 14, a damping element disposed in proximity to the outer end of said tube and said inner end of said passage.

16. An earplug as defined in claim 14, a diaphragm element disposed in proximity to the outer end of said tube and said inner end of said passage and operative to increase attenution in a lower portion of the audible spectrum to obtain a still more uniform attenuation of sounds by the earplug over the audible spectrum.

17. A method of protecting the ear from damaging exposure to high intensity sounds while permitting recognition of sounds, comprising the steps of forming an eartip assembly for insertion in the ear including a central tube surrounded by compressible foam material, restricting passage of sound through said tube to dampen resonances which would otherwise be produced by an intrinsic mass acoustical reactance of said tube and an intrinsic compliance of the earcanal, and extending a passage from an outer end of the tube to a sound inlet to produce a resonant peak at a frequency at which intelligibility of sounds is enhanced and at which said passage has a length that is approximately equal to a quarter wavelength.

18. A method as defined in claim 17, including the additional step of adjusting the length of said passage according to requirements of a particular user or class of users.

19. An earplug as defined in claim 1, said first passage means comprising a sound tube in a custom earmold.

* * * * *